United States Patent [19]

Barzaghi et al.

[11] Patent Number: 4,867,737

[45] Date of Patent: Sep. 19, 1989

[54] DERIVATIVES OF 4-PHENYL-4-OXO-2-BUTENOIC ACID THEIR PREPARATION PROCESS, THEIR USE AS MEDICAMENTS AND COMPOSITIONS CONTAINING THEM

[75] Inventors: Fernando Barzaghi, Monza; Alina Butti, Milan, both of Italy

[73] Assignee: Roussel UCLAF, Paris, France

[21] Appl. No.: 210,170

[22] Filed: Jun. 21, 1988

Related U.S. Application Data

[63] Continuation of Ser. No. 53,688, May 26, 1987, abandoned.

[30] Foreign Application Priority Data

Jun. 6, 1986 [IT] Italy ............................. 20703 A/86

[51] Int. Cl.$^4$ ............................................ C07C 59/90
[52] U.S. Cl. ...................................... 562/463; 560/53
[58] Field of Search ........................... 562/463; 514/545

[56] References Cited

U.S. PATENT DOCUMENTS

| 4,450,292 | 5/1984 | Christidis | 560/53 |
| 4,454,155 | 6/1984 | Christidis | 424/317 |
| 4,594,443 | 6/1986 | Bianchi | 560/53 |

FOREIGN PATENT DOCUMENTS

| 204286 | 10/1986 | European Pat. Off. | 560/53 |
| 2075836 | 11/1981 | United Kingdom | 560/53 |
| 2107714 | 5/1983 | United Kingdom | 560/53 |
| 2108385 | 5/1983 | United Kingdom | 560/53 |

*Primary Examiner*—Paul J. Killos
*Attorney, Agent, or Firm*—Stevens, Davis, Miller & Mosher

[57] ABSTRACT

Compounds of the formula (I):

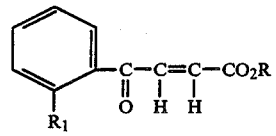

in which $R_1$ represents alkoxy containing from 1 to 8 carbon atoms, and R represents hydrogen or alkyl containing from 1 to 8 carbon atoms, as well as their alkali metal, alkaline-earth metal, ammonium or amine salts, which are useful in the treatment of hyperchlorhydria, gastric or gastroduodenal ulcers, gastritis, hiatal hernias, or gastric or gastroduodenal ailments accompanied by gastric hyperacidity. Also, therapeutic compositions containing the same and method of treating patients suffering from these ailments.

3 Claims, No Drawings

DERIVATIVES OF 4-PHENYL-4-OXO-2-BUTENOIC ACID THEIR PREPARATION PROCESS, THEIR USE AS MEDICAMENTS AND COMPOSITIONS CONTAINING THEM

This application is a continuation of application Ser. No. 053,688, filed May 26, 1987 abandoned.

The present invention is concerned with new derivatives of 4-phenyl-4-oxo-2-butenoic acid, their preparation process, their use as medicaments and compostions containing them.

The subject of the invention is, in all the possible stereoisomeric forms, compounds with the formula (I):

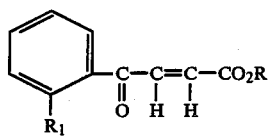

in which $R_1$ represents alkoxy containing from 1 to 8 carbon atoms and R represents hydrogen or alkyl containing from 1 to 8 carbon atoms, as well as their alkali metal, alkaline-earth metal, ammonium or amine salts.

When R represents alkyl, it is preferred to be methyl, ethyl, n-propyl, isopropyl, n-butyl, isobutyl, tertbutyl or n-pentyl.

$R_1$ preferably represents methoxy, ethoxy or n-propoxy.

The products with the formula (I) possess a double bond and can be presented in the form of E or Z isomers; and these various isomers are included, of course, in the scope of the invention.

The alkali metal or alkaine-earth metal salts of the compounds with the formula (I) in which R represents hydrogen can be sodium, potassium, lithium or calcium salts.

The amine salts of the compound with the formula (I) in which R represents a hydrogen atom are the normal amine salts. Among the normal amines, there can be mentioned monoalkylamines, such as, for example, methylamine, ethylamine, propylamine, dialkylamines, such as, for example, dimethylamine, diethylamine, di-n-propylamine, and trialkyl amines, such as triethylamine. There can also be mentioned piperidine, morpholine, piperazine and pyrrolidine.

The subject of the invention is more particularly compounds with the formula (I) as defined previously, in which R represents a hydrogen atom as well as their alkali metal, alkaline-earth metal, ammonium or amine salts, as well as those for which $R_1$ represents a methoxy group.

Among the compounds of the invention, there can be mentioned quite particularly (E) 4-(2-methoxyphenyl)-4-oxo-2-butenoic acid as well as its alkali metal, alkaline-earth metal, ammonium or amine salts.

The experimental part set out hereinafter shows that the compounds of the invention offer much more useful pharmacological properties than 4-phenyl-4-oxo-2-butenoic acid described as a medicament in U.S. Pat. No. 4,473,583.

The compounds with the formula (I) as well as their salts offer useful pharmacological properties. They show a significant anti-ulcer activity in affections of the digestive tract. Furthermore, when they are put into contact with gastric mucous, they show an anti-secretory activity and cyto-protective activity.

These properties justify the use of the compounds with the formula (I), as well as of their pharmaceutically acceptable salts, as medicaments.

Therefore the subject of the invention is, as medicaments, the compounds with the formula (I) as well as their pharmaceutically acceptable alkali metal, alkaline-earth metal, ammonium and amine salts.

The subject of the invention is quite particularly, as a medicament, (E) 4-(2-methoxyphenyl)-4-oxo-2-butenoic acid, as well as its pharmaceutically acceptable alkali metal, alkaline-earth metal, ammonium or amine salts.

The medicaments according to the invention can be used in human or animal therapeutics, in particular in the treatment of hyperchlorhydria, gastric and gastro-duodenal ulcers, gastritis, hiatal hernias, and gastric and gastro-duodenal affections which accompany gastric hyperacidity.

The posology, variable according to the compound used and the affection in question, may range, for example, between 0.05 and 2 g per day in adults, by oral route.

The subject of the present application is also pharmaceutical compositions which contain as the active principle at least one previously mentioned compound. These compositions are made up in such a way that they can be administered by digestive or parenteral route.

They can be solid or liquid, and be presented in the pharmaceutical forms currently used in human or animal medicine, as for example, plain or sugar-coated tablets, gelules, granules, suppositories, and injectable preparations; they are prepared according to the usual methods.

The active principle or principles can be incorporated with excipients usually employed in these pharmaceutical compositions, such as talc, gum arabic, lactose, starch, magnesium stearate, cocoa butter, aqueous or non-aqueous vehicle, fatty substances of animal or vegetable origin, paraffin derivatives, glycols, various moistening, dispersing or emulsifying agents, and preservatives.

The subject of the invention is also a preparation process for compounds with the formula (I), characterized in that glyoxylic acid is reacted with a derivative with the formula (II):

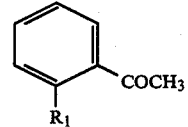

in which $R_1$ is as previously defined, in the presence of a dehydrating agent, so as to obtain the corresponding compound with the formula (I) which is submitted, if desired, either to the action of a base in order to form the salt, or to the action of an esterification agent in order to obtain a compound with the formula (I) in which R represents an alkyl radical containing from 1 to 8 carbon atoms.

Also included in the invention is a variant of the preceding process characterized in that a compound with the formula (III):

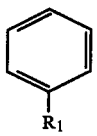 (III)

in which R₁ is as previously defined, is reacted with maleic anhydride in order to obtain the corresponding compound with the formula (I) in which R represents a hydrogen atom.

In a preferred method of realization of the process of the invention:
the dehydration agent is an acid such as, for example, acetic acid;
the base with which, if desired, the compound with the formula (I) in which R represents a hydrogen atom is reacted, is, for example, sodium hydroxide, potassium hydroxide, lithium hydroxide, calcium hydroxide. sodium ethylate, potassium ethylate, ammonia or an amine. such as, for example. methylamine, ethylamine, propylamine, dimethylamine, diethylamine, di-n-propylamine, triethylamine, piperidine, morpholine, piperazine or pyrrolidine;
the reaction with the base is conducted, preferably in a solvent or a mixture of solvents, such as water, ethyl ether, ethanol, acetone or ethyl acetate;
the esterification reaction takes place, for example, by making the acid with the formula (I) react with an alcohol of formula R—OH in an acid medium, for example, in the presence of one of the following acids: hydrochloric, phosphoric or paratoluene sulphonic.

Naturally the esterification can be accomplished according to the other usual methods, such as, for example, by making an acid chloride and alcohol, or acid anhydride and alcohol react together, or by making the acid and the alcohol react in the presence of dicyclohexylcarbodiimide.

In the variant of the process, the reaction between the compound with the formula (III) and the maleic anhydride takes place in the presence of aluminium chloride.

EXAMPLE 1

(E) 4-(2-methoxyphenyl)-4-oxo-2-butenoic acid.

A mixture of 5 g of 2-methoxy acetophenone, 3.06 g of monohydrated glyoxylic acid, 50 cm³ of acetic acid and 5 cm³ of hydrochloric acid is taken to reflux for 8 hours. The solvents are evaporated under reduced pressure, the residue is taken up with ethyl ether, filtered and recrystallized in ether. 2.5 g of expected product is obtained. m.p.=146°–148° C.

PHARMACEUTICAL FORMS

EXAMPLE 2

Tablets

Tablets were prepared having the following formula:
Product of Example 1; 100 mg
Excipient q.s. for a tablet terminated at; 300 mg (Detail of excipient: lactose, wheat starch, treated starch, rice starch, magnesium stearate, talc.)

EXAMPLE 3

Gelules

Gelules were prepared having the following formula:
Product of Example 1; 100 mg
Excipient q.s. for a gelule terminated at; 300 mg
(Detail of excipient: talc, magnesium stearate, aerosil.)

PHARMACOLOGICAL STUDY (1) Determination of the anti-gastric secretory activity.

The technique used is described by H. SHAY et al in *Gastroenterology* 5, 43, 1945.

Male rats are used weighing about 200 g (10 animals per group), deprived of nourishment for 48 hours, but having as much as desired of an 8% glucose solution. The pylorus of the rats is ligatured, the rats having been lightly anesthetized with ether. Then, at the end of the operation, the compounds under test are administered at various doses, or for the control animals, a 0.5% carboxymethyl cellulose solution is administered by intraduodenal route. Then the abdominal incision is sutured.

Three hours later, the animals are killed and their stomachs are removed after ligature of the oesophagus. The gastric juice is removed and centrifuged. Then the volume is measured; and on 100 μl of gastric juice, the total acidity is determined by titration at pH 7 with N/10 sodium hydroxide.

The percentages of variation of total acidity of the gastric secretions are calculated in relation to the results obtained with the control animals.

The results are reported in the table which appears hereafter.

(2) Determination of anti-ulcer activity
Ulcer from stress

The technique consists of inducing ulcers in the stomachs of the rats through stress (constraint and cold.)

The technique used is described by E. C. SENAY and R. J. LEVINE, *Proc. Soc. Exp. Biol.* 124, 1221 (1967).

Female rats weighing 150 g are used (5 animals per group), starved for 48 hours with water "ad libitum" and glucose solution for 8 hours. The animals receive the product under test by a probang, or the control animals receive a 0.5% carboxymethyl cellulose solution.

Two hours later, the animals are wrapped up in a wire-netting jacket, their paws are bound and the whole is placed in a refrigerator at 8° C. for two hours. The rats are freed and killed with ether.

Their stomachs are removed, opened along the greater curvature and examined by means of a binocular magnifier; the seriousness of the lesions is rated from 0 to 3 for each stomach.

For each group of rats the average intensity of the ulcerations is calculated, then for each group the degree of ulceration in relation to the controls is determined.

The results are reported in the table which appears hereafter. Product 1 is the product of Example 1; Product p is the product of Example 1 of U.S. Pat. No. 4,473,583.

(3) Determination of actute toxicity

The lethal dose 50 (LD₅₀) was evaluated after administration of the products by oral route to a mouse.

The results are reported in the table which appears hereafter.

Results

Anti-secretory and anti-ulcer activity (% variation in relation to the controls.)

| PRODUCT | LD$_{50}$ mg/kg | Doses mg/kg | Acid Concentration | Ulceration |
|---|---|---|---|---|
| 1 | 370 | 10 | −78 | −80 |
| p | 250 | 10 | −66 | −54 |

We claim:

1. (E) 4-(2-methoxyphenyl)-4-oxo-2-butenoic acid as well as its alkali metal, alkaline-earth metal, ammonium and amine salts.

2. A method for treating a patient suffering from gastric or gastroduodenal ulcers, comprising:
   administering to said patient a therapeutically effective amount of a compound defined in claim 1 or a pharmaceutically acceptable alkali metal, alkaline-earth metal, ammonium or amine salt thereof.

3. A therapeutic composition for the treatment of a patient suffering from, gastric or gastroduodenal ulcers, comprising a therapeutically effective amount of a compound as defined in claim 1 or a pharmaceutically acceptable alkali metal, alkaline-earth metal, ammonium or amine salt thereof and a pharmaceutically acceptable carrier.

* * * * *